United States Patent [19]

Roemer

[11] Patent Number: 4,957,479

[45] Date of Patent: Sep. 18, 1990

[54] INDWELLING URETERAL STENT PLACEMENT APPARATUS

[75] Inventor: Frederick D. Roemer, Bloomington, Ind.

[73] Assignee: Vance Products Incorporated, Spencer, Ind.

[21] Appl. No.: 258,832

[22] Filed: Oct. 17, 1988

[51] Int. Cl.$^5$ ............................................ A61M 25/00
[52] U.S. Cl. ......................................... 604/8; 604/281
[58] Field of Search ................................... 604/8, 281

[56] References Cited

U.S. PATENT DOCUMENTS

| | | |
|---|---|---|
| 3,938,529 | 2/1976 | Gibbons . |
| 3,995,642 | 12/1976 | Adair . |
| 4,068,660 | 1/1978 | Beck . |
| 4,212,304 | 7/1980 | Finney . |
| 4,250,881 | 2/1981 | Smith . |
| 4,350,161 | 9/1982 | Davis, Jr. ........................... 251/339 |
| 4,531,933 | 7/1985 | Norton et al. ......................... 604/8 |
| 4,571,239 | 2/1986 | Heyman ............................ 604/54 |
| 4,581,019 | 4/1986 | Curelaru et al. ...................... 604/164 |
| 4,610,657 | 9/1986 | Densow ................................. 604/8 |
| 4,610,671 | 9/1986 | Luther ................................. 604/168 |
| 4,643,716 | 2/1987 | Drach ................................. 604/8 |
| 4,671,795 | 6/1987 | Mulchin ............................. 604/281 |
| 4,699,611 | 10/1987 | Bowden ............................. 604/51 |
| 4,713,049 | 12/1987 | Carter ................................. 604/8 |
| 4,757,827 | 7/1988 | Buchbinder et al. ............... 128/772 |
| 4,787,884 | 11/1988 | Goldberg ............................. 604/8 |

Primary Examiner—C. Fred Rosenbaum
Assistant Examiner—C. Maglione
Attorney, Agent, or Firm—Woodard, Emhardt, Naughton, Moriarty & McNett

[57] ABSTRACT

An indwelling ureteral stent positioning apparatus is provided for allowing single intrusion placement of a stent in the ureter of a patient. The apparatus is preassembled and includes a wire guide with floppy tip. The stent is positioned about the wire guide adjacent to the floppy tip of the wire guide, and is adjustably situated on the wire guide to expose a pre-determined length of the floppy tip for insertion into the patient. The stent is a dual open-ended tubular stent having a resilient retentive curved circular or pigtail shape at each end for retention in the kidney and bladder. A positioner is conveyed on the wire stent until the end of the positioned abuts the anatomically distal end of the stent. A pin-vise clamp abuts the external end of the positioner and releasably engages the wire guide to stabilize the apparatus during insertion. When used to position the stent within the ureter, the apparatus is conveyed along the ureter until the floppy tip is within the renal collecting system. The positioner is advanced along the wire guide to push the anatomically proximal end of the stent over and beyond the floppy tip so that the retentive coil forms within the kidney. The pin-vise clamp is released to allow the wire guide to be withdrawn until it passes the anatomically distal end of the stent, wherein the retentive coil shape is formed within the bladder. With the stent fully indwelling, the positioner and wire guide are removed from the patient.

8 Claims, 2 Drawing Sheets

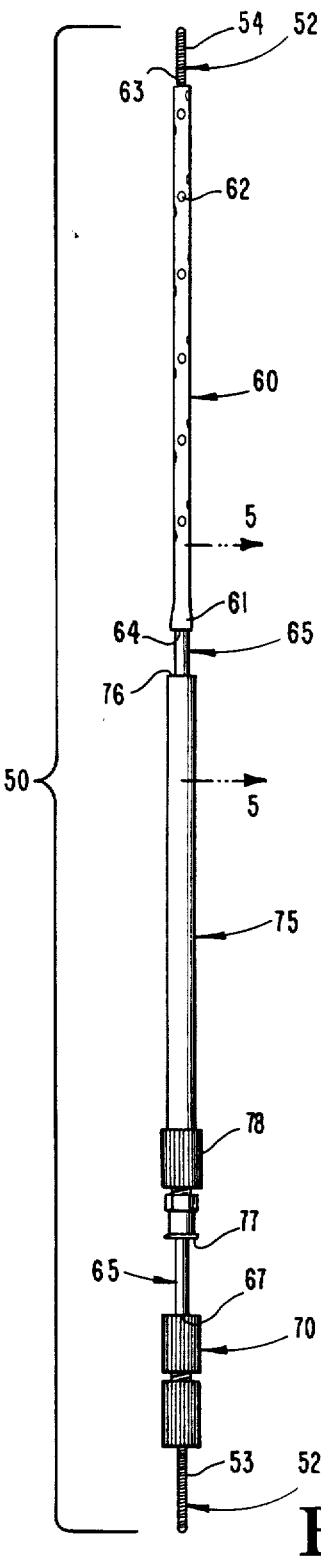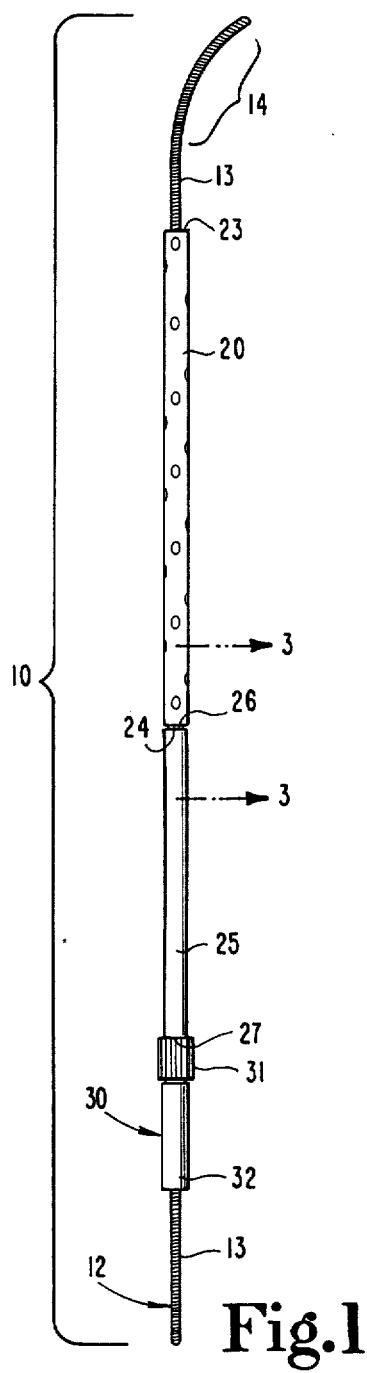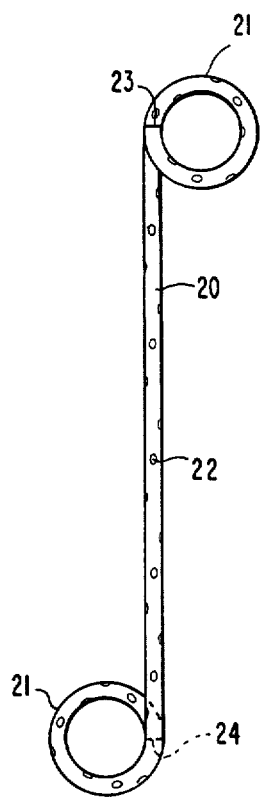
Fig. 1
Fig. 2
Fig. 4

INDWELLING URETERAL STENT PLACEMENT APPARATUS

BACKGROUND OF THE INVENTION

This invention relates to indwelling ureteral stents or drainage tubes for use in bypassing urinary tract obstructions or maintaining the patency of urinary passageways. In particular, the present invention addresses an apparatus for use in the placement of ureteral stents in a patient, whether by antegrade or retrograde placement.

Indwelling ureteral stents have been widely used for the past ten years. These stents are placed in the ureter, which is the duct between the kidney and the bladder, for the express purpose of establishing and/or maintaining an open, patent flow of urine from the kidney to the bladder. The predominant indications for placing a ureteral stent include extrinsic compression occlusions, ureteral injury due to trauma, and obstructive uropathy. The typical ureteral stent can be composed of various radiopaque polymers, including polyethylene, silicone, polyurethane, and thermoplastic elastomer. These stents are retained in the ureter by a retentive curve shape, such as a pigtail, coil, J-shape or hook configuration, at either end of the stent that engages the walls of the bladder and the kidney, respectively The stent is resilient to allow it to be straightened for insertion into a body passageway, and still return to its predetermined retentive curve shape when in situ.

Indwelling ureteral stents are positioned in the ureter by antegrade (percutaneous) placement, retrograde (cystoscopic) placement through the urethra, as well as by open ureterotomy or surgical placement in the ureter by direct manipulative control. Ureteral stent positioning has heretofore been accomplished by two basic methods. In one method, a wire guide is introduced into the ureteral orifice in the bladder via a cystourethroscope under direct vision. The wire guide is advanced up the ureter until the advancing flexible tip of the guide is confirmed by X ray or fluoroscopy to be in the renal pelvis of the kidney. A tubular stent with both ends open is fed onto the exposed external segment of the wire guide and advanced over the wire guide by hand until a short segment of the stent is visible outside the cystoscope. A pusher catheter, "positioner" or length of tubing is then fed onto the exposed external end of the wire guide and advanced over the wire guide by hand until it butts against the stent. With the wire guide held stationary, the positioner is advanced over the wire guide to push the tubular stent up the ureter to the renal pelvis. With the anatomically proximal end of the stent in the renal pelvis, the positioner is held stationary while the wire guide is gradually extracted from the stent and the positioner. As the wire guide leaves the proximal end of the tubular stent, the retentive hook or curve of the proximal end of the stent is formed to retain the stent in the pelvis of the kidney. As the wire guide is withdrawn past the distal, or intravesicle, end of the stent, the retentive hook or curve of the distal end is formed so that the stent end is retained within the bladder. At this point, the positioner and wire guide are completely withdrawn leaving only the stent indwelling in the ureter, bladder and kidney.

In another method of ureteral stent placement, a ureteral stent having one end closed is backloaded onto a wire guide. In this "push-up" method, the tip of the wire guide contacts the closed end of the ureteral stent, which is then introduced into the ureteral orifice in the bladder via a cystourethroscope under direct vision. The stent is advanced up the ureter under fluoroscopic control until the tip of the stent lies within the renal pelvis. A positioner catheter or length of tubing is fed onto the external end of the wire guide and advanced over the wire guide by hand until it butts against the open, distal end of the stent. The positioner is held steady while the wire guide is removed in a fashion similar to that described above.

In the first placement method discussed above, the urinary tract is subject to essentially three invasive entries—once when the wire guide is introduced into the ureteral orifice, again when the tubular stent is advanced over the wire guide, and yet again when the pusher catheter is fed onto the wire guide. In the second "push up" placement method, two invasive entries are required—once when the stent and wire guide is inserted, and again when the positioner is fed along the external end of the wire guide. Moreover, in the second method of placement, a closed end stent is required to be pushed by the end of the wire guide. In this respect, the first method of placement is desirable over the "push up" placement method because a tubular stent may be used that is cheaper and easier to produce, and that provides a more open flowpath from the kidney to the bladder through the open ends of the stent.

In view of the limitations of the prior art ureteral stents and placement methods, it is desirable to provide a indwelling ureteral stent kit that requires only a single invasive entry into the ureteral orifice and ureter, while allowing the use of an open ended tubular stent.

SUMMARY OF THE INVENTION

One embodiment of the invention might include an apparatus for introducing an indwelling ureteral stent into the ureter of a patient. The apparatus includes a wire guide having a flexible tip at its anatomically proximal end for facilitating conveying the apparatus into the ureter of the patient. A ureteral stent, a tubular positioner and a :lamp are serially slidably disposed about the wire guide with the stent adjacent to the flexible end of the wire guide, for insertion of the complete apparatus into the ureter of the patient in a single invasive entry. The stent includes a relatively flexible tubular member having a central lumen opening at both ends of the tubular member and further having end portions at each of the ends that are adapted to resiliently assume a retentive curved shape, when the wire guide is removed from the stent, to retain the stent in an indwelling arrangement. The positioner includes a tubular body having an end abutting the anatomically distal end of the stent and an end accessible external to the patient. The clamp is engaged on the wire guide external to the patient and in abutting relationship with the end of the stent. The clamp includes means for locking the positioner and the stent against motion relative to the wire guide toward the flexible end of the wire guide while the apparatus is being conveyed along the ureter of the patient.

In another embodiment, a method of implanting an indwelling ureteral stent in a patient comprises the initial step of assembling a placement apparatus by serially disposing a tubular stent, a tubular pusher and a releasable clamp in abutting relationship about a wire guide with the anatomically proximal end of the tubular stent adjacent the flexible end of the wire guide. The stent is hollow along its entire length and includes retentive portions at each of the distal and proximal ends of the stent adapted to resiliently assume a curved shape when the wire guide is removed from the stent. The flexible end of the placement apparatus is inserted into the ureter through either the bladder or the kidney of the patient with the clamp engaged on the wire guide. The placement apparatus is advanced along the ureter until the flexible end of the wire guide is situated within either the bladder or the kidney. In the method of this embodiment, the pusher is advanced along the wire guide, while maintaining the position of the clamp and the wire guide relative to the patient, to force the stent along the wire guide through the ureter until the retentive portion at the leading end of the stent is situated within either the bladder or the kidney and has resiliently assumed its curved shape. While maintaining the position of the pusher relative to the patient, the wire guide is retracted from the ureter through the pusher and the stent, until the flexible end of the wire guide has been retracted beyond the retentive portion at the proximal end of the stent and the retentive portion has resiliently assumed its curved shape within either the bladder or the kidney to retain the stent within the ureter. With the stent fully indwelling, the wire guide and pusher are completely retracted from the patient.

It is one object of the present invention to provide an apparatus and method for introducing an indwelling ureteral stent into a patient in a single invasive entry of the patient. It is another object to provide an apparatus that can be used equally well for antegrade or retrograde placement. It is a further object to provide a pre assembled apparatus for introducing an indwelling ureteral stent that allows the use of a tubular stent having open ends and that is readily available for introduction into the patient. Other objects and benefits of the apparatus and method of this invention can be determined on review of the following specification and accompanying figures.

BRIEF DESCRIPTION OF THE DRAWINGS

FIG. 1 is a perspective view of the indwelling ureteral stent placement apparatus of one embodiment of the present invention, which includes the ureteral stent and means for positioning the stent in a patient.

FIG. 2 is an enlarged perspective view of the stent in the configuration that the stent assumes when it is indwelling in the kidney, ureter, and bladder of the patient.

FIG. 4 is a perspective view of the indwelling ureteral stent placement apparatus of another embodiment of the present invention that includes a tapered pusher and a release sheath.

DESCRIPTION OF THE PREFERRED EMBODIMENTS

Figure 3:
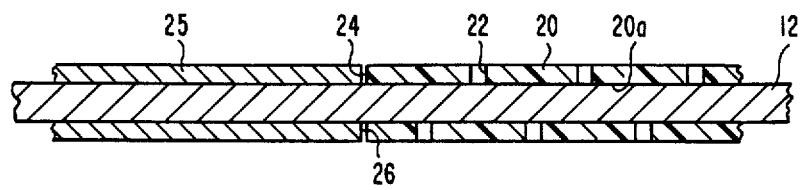
FIG. 3 is an enlarged sectional view of the ureteral stent placement apparatus of FIG. 1, taken along line 3—3 as viewed in the direction of the arrows.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In one embodiment of the present invention, an indwelling ureteral stent placement apparatus 10 includes a stylet or wire guide 12, having a relatively rigid main body 13 and a flexible, or floppy, tip 14. The wire guide 12 is sufficiently rigid for introduction into the ureteral orifice of the bladder via a cystourethroscope, and for advancement up the ureter into the renal pelvis of the kidney. The wire guide 12 in the preferred embodiment has a length of about 145 mm and a 0.038 inch diameter. The preferred wire guide is composed of TEFLON ®-coated stainless steel and has a tapered mandril construction to provide a floppy tip 14 of approximately 3 cm in length, such as the wire guide Part No. 638433 sold by Cook Urological Co. In use, the floppy tip 14 functions as or similarly to a filiform tip, which is a thin, flexible catheter-like length of plastic that is particularly useful in negotiating passage through the urethra and prostate gland to enter the bladder in a male patient. The floppy tip 14 is used to guide the indwelling ureteral stent placement apparatus through the ureter and into the renal pelvis of the kidney.

The placement apparatus 10 includes a tubular stent 20 having a central lumen 20a (FIG. 3) and open ends 23 and 24. For clarity, end 23 is referred to herein as the proximal end 23 of the stent because when the stent is inserted into the patient, the end 23 is the first end inserted and is anatomically proximal to the kidney (in a transcystoscopic placement). Conversely, the end 24 is referred to alternatively as the distal end 24. Employing this convention, the wire guide and placement apparatus are inserted at their respective anatomically proximal ends, while the distal end of the wire guide is externally accessible to the physician or operator for manipulation. The stent 20 includes a plurality of apertures 22 passing through the wall of the tubular stent 20 to the central lumen 20a (FIG. 3). The central lumen 20a and the apertures 22 provide a patent flowpath for renal fluids from the kidney to the bladder.

The stent 20 assumes a pre-determined retentive curved shape 21 at each of the ends 23 and 24, as illustrated in FIG. 2. The stent is sufficiently flexible to allow the curve shapes 21 to be straightened for insertion into the ureter, but is sufficiently elastic or resilient so as to resume the curved shape once the stent is in situ. The retentive curve 21 of the proximal end 23 is engaged within the kidney, while the retentive curve 21 of the distal end 24 is situated at the bladder in a conventional fashion once the stent is indwelling. In the preferred embodiment, the ends of the stent define a "pigtail" configuration at either end. One such stent is the Multi-Length Ureteral Stent composed of radiopaque polyurethane, produced by Cook Urological, which has about 2 ½ 360° coils at each end of the stent. Other such stents having retentive curve shapes at the ends may have up to 8 coils at one end of the stent, or may have as little as one half of a coil—i.e., a 180° hook.

In the present invention, the elements of the placement apparatus 10 are pre-assembled and provided to the operator as a complete ready to-use unit. In assembling the apparatus 10, one end of the dual open-ended ureteral stent 20 is loaded onto the stiff main body 13 of the wire guide 12. The stent is advanced along the main body until the entire length of the stent 20 is positioned on the wire guide, at which point the retentive curves 21 at each end are straightened out. The stent 20 is manually advanced toward the floppy tip 14 of the wire guide until only a desired length of the floppy tip extends beyond the proximal end 23 of the stent. When the placement apparatus 10 of the preferred embodiment is being prepared, the entire 3 cm length of the flexible tip 14 may extend beyond the proximal end 23 of the stent, for example. On the other hand, the proximal end 23 of the stent 20 may be partially advanced onto the floppy tip 14 so that less than the 3 cm length of the floppy tip is exposed beyond the stent. In this case, the retentive curve 21 at the proximal end 23 of the stent may partially form since the floppy tip 14 adds less resistance to the resilient behavior of the retentive coil 21 than the stiffer main body 13 of the wire guide 12. Positioning the proximal end 23 of the stent 20 at any location short of the end of the floppy portion 14 results in the establishment of a "filiform"-like guide tip for relatively atraumatic advancement and placement of the stent in the ureter. In the preferred embodiment, the stent 20 is positioned on the wire guide 12 with the proximal end 23 of the stent 20 between 3 and 5 centimeters from the free end of the floppy portion 14.

With the tubular stent 20 in position on the wire guide 12, a tubular pusher or positioner 25 is advanced onto the main body 13 of the wire guide until the end 26 of the positioner butts against the anatomically distal end 24 of the tubular stent 20. The preassembly of the indwelling ureteral stent placement apparatus 10 is completed by feeding a clamp 30 onto the wire guide until it butts against the end 27 of the positioner 25 farthest from the stent 20. The clamp 30 may comprise a locking pin-vise clamp or a stabilizing clip, which will grip the wire guide adjacent the external end 27 of the positioner 25 to prevent slippage or dislodgement of the positioner 25 and stent 20 along the wire guide 12. The clamp 30 includes a releasable locking vise 31 and an integral handle 32. The clamp 30, and more particularly, the pin vise clamp 31, may consist of a locking collet or an O-ring type device. In the preferred embodiment, the clamp 30 comprises a pin vise marketed by Cook Urological, of Spencer, Ind., as Part No. PPV-100. With the locking clamp 30 in place, the placement apparatus 10 represents a complete assembly for immediate insertion into the urinary tract of the patient.

The indwelling ureteral stent placement apparatus 10 of the present invention provides a less intrusive way of positioning the stent 20 in the ureter of a patient than the devices of the prior art. Unlike the earlier positioning methods, the placement apparatus 10 of the present invention requires only one entry, rather than two or three entries, into the urinary tract of the patient. In a retrograde placement, the floppy tip 14 of the wire guide 12 is advanced under direct vision transcystoscopically into the ureteral orifice of the bladder and up the ureter under X ray or fluoroscopic control, with the clamp 30 in its locked configuration to stabilize the apparatus The floppy tip assists in negotiating apparatus through the ureter until the tip enters the renal pelvis of the kidney. In a single transcystoscopic operation, the wire guide 12, the tubular stent 20, and the positioner 25 are situated within the urinary tract with part of the wire guide and positioner being externally accessible. During the insertion, the stent 20 and positioner 25 react against the clamp 30 that is locked onto the wire guide 12 to prevent the stent and positioner from sliding off of the wire guide 12. Once the floppy tip 14 is well within the kidney, the positioner 25 is advanced along the wire guide 12 to push the stent 20 over the floppy tip 14, thus allowing the retentive curve 21 to form in the kidney at the proximal end 23 of the stent. The positioner 25 is then held stationary while the wire guide 12 is removed. When the wire guide passes the anatomically distal, or intravesicle, end 24 of the tubular stent 20, the retentive curve 21 forms at the end 24 to retain the stent 20 lodged within the bladder. With the stent 20 in its indwelling position, the positioner and wire guide is removed.

In many procedures using the indwelling ureter stent placement apparatus 10 of the present invention, the length of the floppy tip 14 must be adjusted to a specific length to facilitate negotiating the urinary tract of a patient. Once the proximal end of the apparatus passes beyond the cystoscope. greater or lesser flexibility may be required at the floppy tip 14. For instance, in negotiating a curved portion of the ureter, advisable to release the locking device 31 of the clamp 30 to push the positioner 25 and the stent 20 farther up the wire guide 12 toward the floppy tip 14. When the retentive curve portion 21 of the proximal end 23 of the stent reaches the floppy tip 14, it will assume a portion of its retentive curved shape. This partially formed curve at the end of the wire guide 12 may provide means for steering the placement apparatus 10 along the ureter of the patient. Once the placement apparatus 10 has negotiated the curve of the ureter, the locking device 31 can be released and the clamp 30 moved toward the external end of the wire guide 12 to allow the positioner 25 and stent 20 to move over and away from the floppy tip 14 of the wire guide 12.

Figure 5:
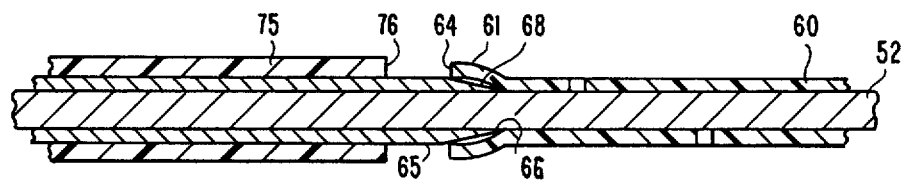
FIG. 5 is an enlarged sectional view of the ureteral stent placement apparatus of FIG. 4, taken along line 5—5 as viewed in the direction of the arrows.

In another embodiment of the present invention, illustrated in FIGS. 4 and 5, a ureteral stent positioning apparatus 50 includes a wire guide 52 having a main body 53 and a flexible tip 54. The wire guide 52 is similar in construction to the wire guide 12 of the previous embodiment, with the exception that the flexible tip in the preferred design is 1 cm in length. A dual open-ended tubular stent 60 is situated about the wire guide adJacent the proximal floppy tip 54. The stent 60 includes a central lumen 60a along its length from the open distal end 64 to the open proximal end 63, and also includes a plurality of apertures 62 opening into the central lumen. The stent 60 in this embodiment is identical to the stent 20 described above.

In this second embodiment, however, the positioner 65 includes a taper 68 at its proximal end. When assembled on the wire guide 52, the taper 68 is advanced about 2-3 mm into the anatomically distal end 64 of the stent 60, forming an enlarged region 61 in the stent due to its elastomeric properties. The positioner 65 and stent 60 are temporarily locked at the enlarged region 61 at least during insertion of the apparatus 50 into the ureter. In a further variation from the first embodiment, a release sheath 75 is advanced over the wire stent 52 and over the positioner 65 until the end 76 of the release sheath 75 is near the end 64 of the stent. The release sheath is shorter in length than the positioner 65. The sheath 75 may include a clamp 78 at its external end 77 to engage the positioner 65 during insertion. The assembly of the ureteral stent positioning apparatus 50 is completed by the placement of a pin vise clamp 70 over the external end of the wire guide 52 and abutting the external end 67 of the pOsitioner 65. The pin-vise clamp 70 is identical to the clamp 30 and serves the same stabilizing function for the apparatus 50 during the transcystoscopic operation.

The apparatus 50 of this second embodiment is used in a manner similar to the previous apparatus 10. In a single transcystoscopic operation, the apparatus 50 is advanced under direct vision into the ureter until the flexible tip 54 of the wire guide is situated well within the renal collecting system (or the bladder in an antegrade approach). The pin-vise clamp 70 is released to allow the wire guide to be withdrawn sufficiently to allow the retentive coil at the anatomically proximal end 63 of the stent 60 to form in the renal pelvis. While the positioner and wire guide are held, the release sheath 75 is gently advanced along the positioner 65 until tactile feel indicates that the end 76 of the sheath is abutting the end 64 of the stent. With the release sheath 75 stabilized, the positioner 65 is withdrawn to release the taper 68 of the positioner from the enlarged region 61 of the stent. The elasticity of the stent restores the region 61 to its normal shape on:e the positioner has been removed.

Once the positioner is disengaged from the stent, the wire guide can be further removed while the release sheath 75 is stabilized until the wire guide 52 passes the anatomically distal end 64 of the stent to allow the retentive coil to form in the bladder. The wire guide 52, positioner 65 and release sheath 75 are then completely removed from the patient, leaving the ureteral stent 60 wholly indwelling in the ureter, kidney and bladder.

The positioning apparatus 10 and 50 of the present invention are useful in either retrograde of antegrade placement of ureteral stents. With both apparatus, only a single invasion of the patient's urinary tract is required, rather than insertions in consecutive steps of a wire guide, stent end pusher. Moreover, the apparatus of this invention allow use of dual open-ended tubular stents, as opposed to the closed-end stents of some prior art devices. Unlike devices of the prior art, the apparatus 10 and 50 are pre-assembled, adjustable devices for insertion and placement of ureter stents.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An apparatus for introducing an indwelling ureteral stent into the ureter of a patient comprising:
   a wire guide having a distal end and a proximal end, said proximal end including means for facilitating conveying the apparatus into the ureter of the patient;
   a ureteral stent, a tubular positioner and a clamp serially slidably disposed about said wire guide with said stent adjacent said proximal end of said wire guide;
   wherein said stent includes a relatively flexible tubular member having corresponding distal and proximal ends and a central lumen open at each of said ends of said tubular member with said wire guide passing therethrough, and further having end portions at each of said ends of said member, each of said end portions adapted to resiliently assume a curved shape when said wire guide is removed from said each of said end portions to retain said stent in an indwelling arrangement;
   wherein said positioner includes a tubular body having a first end abutting said distal end of said stent, and a second end accessible external to the patient when said proximal end of said wire guide is situated at the renal end of the ureter;
   further wherein said clamp is engaged on said wire guide external to the patient and in abutting relationship with said second end of said positioner, said clamp including means for locking said positioner and said stent against motion relative to said wire guide toward said distal end of said wire guide while said apparatus is being conveyed along the ureter of the patient;
   wherein said positioner includes a tapered tip at one end of said positioner; and
   said tubular member includes a radially expandable portion at said distal end of the member,
   whereby, said tapered tip of said positioner is removably received within said portion of said member when said stent and said positioner are disposed on said wire guide;
   said apparatus further comprising a tubular sheath slidably disposed about said positioner, said sheath having a length less than the length of said positioner and end for contacting said distal end of said stent,
   whereby when said sheath is stabilized, said distal end of said stent reacts against said end of said sheath when said tapered tip of said positioner is removed from said radially expandable portion of said stent.

2. The apparatus of claim 1, wherein:
   said clamp includes means for adjusting the position of said stent and said positioner on said wire guide so that said proximal end of said stent is disposed over a portion of said predetermined length of said flexible tip.

3. The apparatus of claim 1 further comprising a second clamp releasably engaged about said positioner and abutting the distal end of said sheath to lock said sheath against motion relative to said positioner toward the distal end of said positioner while said apparatus is being conveyed along the ureter of the patient.

4. The apparatus of claim 1, wherein said means for facilitating conveying includes a flexible tip having a predetermined length measured from said proximal end of said wire guide.

5. A method of implanting an indwelling ureteral stent in a patient, comprising the steps of:
   assembling a placement apparatus by serially disposing a tubular stent, a tubular pusher and a releasable clamp in end-to-end abutting relationship about a wire guide with the proximal end of the tubular stent adjacent the anatomically proximal end of the wire guide, wherein the stent is hollow along its entire length and includes retentive portions at each of the distal and proximal ends of the stent adapted to resiliently assume a curved shape when the wire guide is removed from the stent;
   inserting the proximal end of the placement apparatus into the ureter through one of the bladder or the kidney of the patient with the clamp engaged on the wire guide;
   advancing the placement apparatus along the ureter until the proximal end of the wire guide is situated within the other of the bladder or the kidney;

advancing the pusher along the wire guide, while maintaining the position of the clamp and the wire guide relative to the patient, to force the stent along the wire guide through the ureter until the retentive portion at the proximal ends of the stent is situated within the other of the bladder or the kidney and has resiliently assumed its curved shape;

retracting the wire guide form the ureter through the pusher and the stent, while maintaining the position of the pusher relative to the patient, until the flexible end of the wire guide has retracted beyond the retentive portion at the distal end of the stent and the retentive portion has resiliently assumed its curved shape within one of the bladder or the kidney to retain the stent within the ureter;

completely retracting the clamp, wire guide and pusher with the stent fully indwelling, wherein said wire guide includes a relatively flexible tip portion of predetermined length from the proximal end of the wire guide; and said step of serially disposing includes adjustably positioning a segment of the retentive portion at the proximal end of the stent about a portion of the predetermined length of the flexible tip so that the retentive portion begins to assume its curved shape.

6. A method of implanting an indwelling ureteral stent in a patient, comprising the steps of:

assembling a placement apparatus by serially disposing a tubular stent, a tubular pusher and a releasable clamp in end-to-end abutting relationship about a wire guide with the proximal end of the tubular stent adjacent the anatomically proximal end of the wire guide, wherein the stent is hollow along its entire length and includes retentive portions at each of the distal and proximal ends of the stent adapted to resiliently assume a curved shape when the wire guide is removed from the stent;

inserting the proximal end of the placement apparatus into the ureter through one of the bladder or the kidney of the patient with the clamp engaged on the wire guide;

advancing the placement apparatus along the ureter until the proximal end of the wire guide is situated within the other of the bladder or the kidney;

advancing the pusher along the wire guide, while maintaining the position of the clamp and the wire guide relative to the patient, to force the stent along the wire guide through the ureter until the retentive portion at the proximal end of the stent is situated within the other of the bladder or the kidney and has resiliently assumed its curved shape;

retracting the wire guide from the ureter through the pusher and the stent, while maintaining the position of the pusher relative to the patient, until the flexible end of the wire guide has retracted beyond the retentive portion at the distal end of the stent and the retentive portion has resiliently assumed its curved shape within one of the bladder of the kidney to retain the stent within the ureter;

completely retracting the clamp, wire guide and pusher with the stent fully indwelling, wherein said wire guide includes a relatively flexible tip portion of predetermined length from the proximal end of the wire guide; and said step of advancing the placement apparatus along the ureter includes the steps of;

disengaging the clamp from the wire stent;

advancing the clamp along the wire guide to force the pusher and the stent along the wire guide until a segment of the retentive portion at the proximal end of the stent is positioned about a portion of the predetermined length of the flexible tip to reduce the relative flexibility of the flexible tip; and p2 re-engaging the clamp about the wire stent.

7. A method of implanting an indwelling ureteral stent in a patient, comprising the steps of:

assembling a placement apparatus by serially disposal a tubular stent, a tubular pusher and a releasable clamp in abutting relationship about a wire guide with the proximal end of the tubular stent adjacent the anatomically proximal end of the wire guide, wherein the stent is hollow along its entire length and includes retentive portions at each of the distal and proximal ends of the stent adapted to resiliently assume a curved shape when the wire guide is removed from the stent;

inserting the proximal end of the placement apparatus into the ureter through one of the bladder or the kidney of the patient with the clamp engaged on the wire guide;

advancing the placement apparatus along the ureter until the proximal end of the wire guide is situated within the other of the bladder or the kidney;

advancing the pusher along the wire guide, while maintaining the position of the clamp and the wire guide relative to the patient, to force the stent along the wire guide through the ureter until the retentive portion at the proximal end of the stent is situated within the other of the bladder or the kidney and has resiliently assumed its curved shape;

retracting the wire guide from the ureter through the pusher and the stent, while maintaining the position of the pusher relative to the patient, until the flexible end of the wire guide has retracted beyond the retentive portion at the distal end of the stent and the retentive portion has resiliently assumed its curved shape within one of the bladder or the kidney to retain the stent within the ureter; and completely retracting the clamp, wire guide and pusher with the stent fully indwelling;

wherein the pusher includes a tapered tip at one end; the step of serially disposing includes;

inserting the tapered tip of the pusher into the central lumen at the distal end of the stent; and disposing a tubular sheath about the pusher, the tubular sheath having a length less than the length of the pusher.

8. A method of implanting an indwelling ureteral stent in a patient, comprising the steps of:

assembling a placement apparatus by serially disposing a tubular stent, a tubular pusher and a releasable clamp in abutting relationship about a wire guide with the proximal end of the tubular stent adjacent the anatomically proximal end of the wire guide, wherein the stent is hollow along its entire length and includes retentive portions at each of the distal and proximal ends of the stent adapted to resiliently assume a curved shape when the wire guide is removed from the stent;

inserting the proximal end of the placement apparatus into the ureter through one of the bladder or the kidney of the patient with the clamp engaged on the wire guide;

advancing the placement apparatus along the ureter until the proximal end of the wire guide is situated within the other of the bladder or the kidney;

advancing the pusher along the wire guide, while maintaining the position of the clamp and the wire guide relative to the patient, to force the stent along the wire guide through the ureter until the retentive portion at the proximal end of the stent is situated within the other of the bladder or the kidney and has resiliently assumed its curved shape;

retracting the wire guide from the ureter through the pusher and the stent, while maintaining the position of the pusher relative to the patient, until the flexible end of wire guide has retracted beyond the retentive portion at the distal end of the stent and the retentive portion has resiliently assumed its curved shape within one of the bladder or the kidney to retain the stent within the ureter; and completely retracting the clamp, wire guide and pusher with the stent fully indwelling;

the method further comprising after the step of advancing the pusher along the wire guide, the steps of;

abutting the ends of the sheath against the distal end of the stent;

retracting the pusher through the sheath, while maintaining the position of the sheath relative to the patient, thereby disengaging the tapered tip of the pusher from the central lumen of the stent.

* * * * *

UNITED STATES PATENT AND TRADEMARK OFFICE
CERTIFICATE OF CORRECTION

PATENT NO. : 4,957,479

DATED : September 18, 1990

INVENTOR(S) : Frederick D. Roemer

It is certified that error appears in the above-identified patent and that said Letters Patent is hereby corrected as shown below:

In column 3, line 32, please change "pre" to --pre- --.
In column 6, line 17, please change "." to --,--.
In column 6, line 19, please insert --it may be-- before "advisable".
In column 6, line 67, please change "pOsitioner" to --positioner--.
In column 7, line 20, please change "on:e" to --once--.
In column 7, line 36, please change "end" to --and--.
In column 10, line 7, please delete "p2" and make the next clause --re-engaging the clamp about the wire stent.-- a new paragraph.

Signed and Sealed this

Fourth Day of February, 1992

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,957,479
DATED : September 18, 1990
INVENTOR(S) : Frederick D. Roemer It is certified that error appears in the above-identified patent and that said Letters Patent is hereby corrected as shown below:

ABSTRACT, beginning on line 11, delete

"A positioner is conveyed on the wire stent until the end of the positioned abuts the anatomically distal end of the stent."

and insert --A positioner is conveyed on the wire guide until the end of the positioner abuts the anatomically distal end of the stent.--

Signed and Sealed this

Fourteenth Day of October, 1997

*Attest:*

BRUCE LEHMAN

*Attesting Officer*     *Commissioner of Patents and Trademarks*